US010898367B2

(12) United States Patent
Nelson

(10) Patent No.: US 10,898,367 B2
(45) Date of Patent: Jan. 26, 2021

(54) URINE BOTTLE

(71) Applicant: VERNACARE LIMITED, Bolton (GB)

(72) Inventor: Wayne Nelson, Radcliffe (GB)

(73) Assignee: VERNACARE LIMITED, Bolton (GB)

( * ) Notice: Subject to any disclaimer, the term of this patent is extended or adjusted under 35 U.S.C. 154(b) by 331 days.

(21) Appl. No.: 14/766,732

(22) PCT Filed: Feb. 7, 2014

(86) PCT No.: PCT/GB2014/050373
§ 371 (c)(1),
(2) Date: Aug. 7, 2015

(87) PCT Pub. No.: WO2014/122475
PCT Pub. Date: Aug. 14, 2014

(65) Prior Publication Data
US 2015/0366699 A1    Dec. 24, 2015

(30) Foreign Application Priority Data
Feb. 8, 2013    (GB) .................................. 1302277.7

(51) Int. Cl.
*A61F 5/455* (2006.01)
*A61G 9/00* (2006.01)
*A61G 7/02* (2006.01)

(52) U.S. Cl.
CPC .............. *A61F 5/455* (2013.01); *A61G 9/006* (2013.01); *A61G 7/02* (2013.01); *A61G 2200/12* (2013.01)

(58) Field of Classification Search
CPC .......... A61F 5/455; A61F 5/453; A61F 5/451; A61F 5/441; A61F 5/4556; A61F 5/48;
(Continued)

(56) References Cited

U.S. PATENT DOCUMENTS

| 698,419 A | 4/1902 | Taylor |
| 897,434 A | 9/1908 | Waltz |

(Continued)

FOREIGN PATENT DOCUMENTS

| FR | 2778842 | 11/1999 |
| GB | 456939 A | 11/1936 |

(Continued)

OTHER PUBLICATIONS

International Search Report and Written Opinion dated May 22, 2014 for International Application No. PCT/GB2014/050373 from European Patent Office, pp. 1-12, Risjswijk, Netherlands.

(Continued)

*Primary Examiner* — Nicholas J Weiss
*Assistant Examiner* — Gabriella E Burnette
(74) *Attorney, Agent, or Firm* — Sherman IP LLP; Kenneth L. Sherman; Hemavathy Perumal

(57) ABSTRACT

A disposable urine bottle, having a front end for presentation to a user comprises a base wall, an enclosing wall extending upwardly from the base wall, a urine receiving volume defined by the base wall and the enclosing wall, and an aperture located above the base wall and which is upwardly and forwardly concave when viewed from the side. The lowermost portion of the aperture is also parallel to the base wall. The enclosing wall has a portion which overhangs the base wall at the front end of the bottle. The aperture is elongate in plan view and the enclosing wall extends outwardly from the sides and front end of the aperture. The maximum width of the aperture is at least half the maximum width of the base wall, and the enclosing wall is formed into a handle portion at one end of the bottle.

22 Claims, 3 Drawing Sheets

(58) Field of Classification Search
CPC ...... A61G 9/006; A61G 7/02; A61G 2200/12; A61G 9/00; A61B 10/007; B65D 1/40
See application file for complete search history.

(56) References Cited

U.S. PATENT DOCUMENTS

| | | | |
|---|---|---|---|
| 967,638 A | 8/1910 | Hogan | |
| 1,296,713 A | 3/1919 | Thieringer | |
| 2,132,651 A | 10/1938 | Schack | |
| 2,582,398 A * | 1/1952 | Siegenthal | A61G 9/006 4/144.1 |
| 3,700,096 A * | 10/1972 | Reifers | B65D 1/34 229/162.4 |
| 3,727,244 A * | 4/1973 | Collins | A61G 9/006 4/144.3 |
| 4,187,562 A * | 2/1980 | Mioduski | A61G 9/006 4/144.3 |
| 5,007,116 A | 4/1991 | Yamamoto | |
| 5,687,429 A * | 11/1997 | Rahlff | A61F 5/455 4/144.4 |
| 6,941,587 B1 * | 9/2005 | Fletcher | A61G 9/006 4/144.1 |
| 2003/0028959 A1 | 2/2003 | Moser | |
| 2011/0113544 A1 * | 5/2011 | Stekloff | A61G 9/003 4/455 |

FOREIGN PATENT DOCUMENTS

| | | | | |
|---|---|---|---|---|
| GB | 2156211 A | | 10/1985 | |
| GB | 2164553 A | | 3/1986 | |
| GB | 2164553 A | * | 3/1986 | ............. A61G 9/006 |
| GB | 2174330 A | | 11/1986 | |
| GB | 2281864 A | | 3/1995 | |
| GB | 2281864 A | * | 3/1995 | ........... A61F 5/4556 |
| GB | 2437251 A | * | 10/2007 | ............. A61G 9/006 |
| GB | 2437251 A | * | 10/2007 | ............. A61G 9/006 |
| JP | 2003325592 A | | 11/2003 | |
| WO | WO-9413242 A2 | * | 6/1994 | ............. A61G 9/006 |

OTHER PUBLICATIONS

United Kingdom Search Report dated Jan. 3, 2014 for UK Application No. GB1302277.7 from United Kingdom Intellectual Property Office, pp. 1-3, South Wales, United Kingdom.

United Kingdom Search Report dated May 15, 2013 for UK Application No. GB1302277.7 from United Kingdom Intellectual Property Office, pp. 1-6, South Wales, United Kingdom.

* cited by examiner

URINE BOTTLE

The present invention relates to urine bottles and in particular, but not exclusively, to disposable female urine bottles.

Women who are confined to bed, for example, female orthopedic patients or females suffering from road accident injuries, hip injuries, multiple sclerosis and the like may, in some circumstances, find it difficult or impossible to sit up in bed or indeed it may prove dangerous to their health to sit up in bed. Such patients will be unable to use a normal bedpan and must utilise either a urine bottle or a "slipper" bedpan (a bedpan having a reduced height to allow it to be positioned more easily beneath the patient), both of which can be used while the patient is either lying or semi-recumbent position. The use of a female urine bottle is preferred to that of a slipper bedpan when only urine is required to be passed by the patient, as it is more comfortable, both physically and psychologically, for the patient.

Two known female urine bottles are disclosed in GB 2164553A and GB 2437251A. In each case, the urine bottle is manufactured from dried, moulded paper pulp and can therefore be disposed of in a macerator after use, which reduces the likelihood of cross-infection as compared with reusable urine bottles.

In accordance with a first aspect of the present invention, there is provided a urine bottle comprising a base wall, an enclosing wall extending upwardly from the base wall, a urine receiving volume defined by the base wall and the enclosing wall and an aperture in the enclosing wall which allows access to the urine receiving volume, the urine bottle being elongate and comprising a front end for presentation to a user, the enclosing wall comprising a portion which overhangs the base wall at the front end of the bottle.

The provision of an overhanging portion at the front end of the bottle forms a "toe" portion which is positioned beneath a user and which is of a significantly lower height than the prior art products, thereby making it easier and more comfortable to use and further reducing the likelihood of leakage during use.

In accordance with a second aspect of the present invention, there is provided a urine bottle comprising a base wall, an enclosing wall extending upwardly from the base wall, a urine receiving volume defined by the base wall and the enclosing wall and an aperture in the enclosing wall which allows access to the urine receiving volume, the aperture being elongate in plan view and comprising front and rear ends and sides joining the front and rear ends, the enclosing wall extending outwardly from the sides and the front end of the aperture.

The provision of an enclosing wall which extends outwardly from the sides and the front end of the aperture results in a bulbous portion which is significantly more comfortable for a user. In addition, such an enclosing wall results in an overhang around the sides and front end of the aperture, which reduces the likelihood of spillage from the aperture when the used bottle is removed and transported.

In accordance with a third aspect of the present invention, there is provided a urine bottle comprising a base wall, an enclosing wall extending upwardly from the base wall, a urine receiving volume defined by the base wall and the enclosing wall and an aperture in the enclosing wall which allows access to the urine receiving volume, the urine bottle being elongate and further comprising handle means at one end.

The provision of a handle means at one end of the bottle significantly facilitates handling of the bottle, both by a user and by a nurse or other helper.

This makes it easier and more convenient for a patient to use, which is important from both a physical and a psychological point of view. The provision of handle means at one end of the bottle also facilitates removal and carrying of the bottle after use, which reduces the likelihood of spillage of urine.

In accordance with a fourth aspect of the present invention there is provided a urine bottle comprising a base wall, an enclosing wall extending upwardly from the base wall, a urine receiving volume defined by the base wall and the enclosing wall and an aperture in the enclosing wall which allows access to the urine receiving volume, the urine bottle being elongate and the width of the aperture at its widest point being at least half the width of the base wall at its widest point.

The provision of an access aperture which is at least half as wide as the greatest width of the base wall significantly reduces the likelihood and incidence of urine leakage during use.

In accordance with a fifth aspect of the present invention, there is provided a urine bottle comprising a base wall, an enclosing wall extending upwardly from the base wall, a urine receiving volume defined by the base wall and the enclosing wall and an aperture in the enclosing wall which allows access to the urine receiving volume, the base wall being substantially planar, the aperture being upwardly concave when viewed from the side and the lowermost portion of the aperture being substantially parallel to the base wall.

The provision of an upwardly concave aperture (when viewed from the side) having a lowermost portion which is substantially parallel to the base wall makes the bottle significantly more comfortable for a user and again further reduces the likelihood and incidence of leakage during use.

Where a handle means is provided, preferably the handle means comprises an end portion of the enclosing wall.

In one embodiment, the base wall is substantially planar and the end portion of the enclosing wall which forms part of the handle means extends substantially perpendicularly to the base wall.

The handle means may comprise one or more inwardly-directed recesses in the enclosing wall. Preferably, there are two inwardly-directed recesses located on opposite sides of the bottle. In a preferred embodiment, the two inwardly-directed recesses are substantially mirror images of each other.

The or each recess is preferably located forwardly of the end wall portion which forms part of the handle means.

The handle means may further comprise a top wall portion of the enclosing wall. The top wall portion preferably extends between two side wall portions of the enclosing wall. The top wall portion also preferably extends towards the aperture, for example towards an upper end of the aperture.

Where the urine bottle is elongate and comprises a front end for presentation to a user and the enclosing wall comprises a portion which overhangs the base wall of the front end of the bottle, preferably the overhanging portion of the enclosing wall extends rearwardly to the front portion of the periphery of the aperture.

The enclosing wall may comprise a portion which overhangs the base wall at the front and side portions of the aperture.

The base wall may be substantially planar and the front most portion of the enclosing wall may meet the base wall substantially perpendicularly.

Preferably, the or each overhanging portion is rounded.

Preferably, the maximum length of the base wall is at least four times as long as the maximum length of the portion of the enclosing wall which overhangs the base wall at the front end of the bottle.

Preferably, the urine bottle is elongate and the width of the aperture at its widest point is at least half the width of the base wall at its widest point.

Where the base wall is substantially planar, the aperture is upwardly concave when viewed from the side and the lowermost portion of the aperture is substantially parallel to the base wall, preferably the aperture is elongate in plan view and comprises front and rear ends and sides joining the front and rear ends, the enclosing wall extending outwardly from the sides and the front end of the aperture.

Preferably, the enclosing wall extends outwardly from the sides and front end of the aperture and downwardly to meet the base wall.

Preferably, in use, the bottle rests on the base wall.

Preferably, the aperture is upwardly and forwardly concave when viewed from the side.

Preferably, the aperture is located above the base wall.

Preferably, the enclosing wall comprises a portion which is located above the base wall rearwardly of the aperture.

Preferably, the urine bottle is formed from maceratable material, for example, dried, moulded paper pulp.

By way of example only, a specific embodiment of the present invention will now be described with reference to the accompanying drawings, in which.

Figure 1:
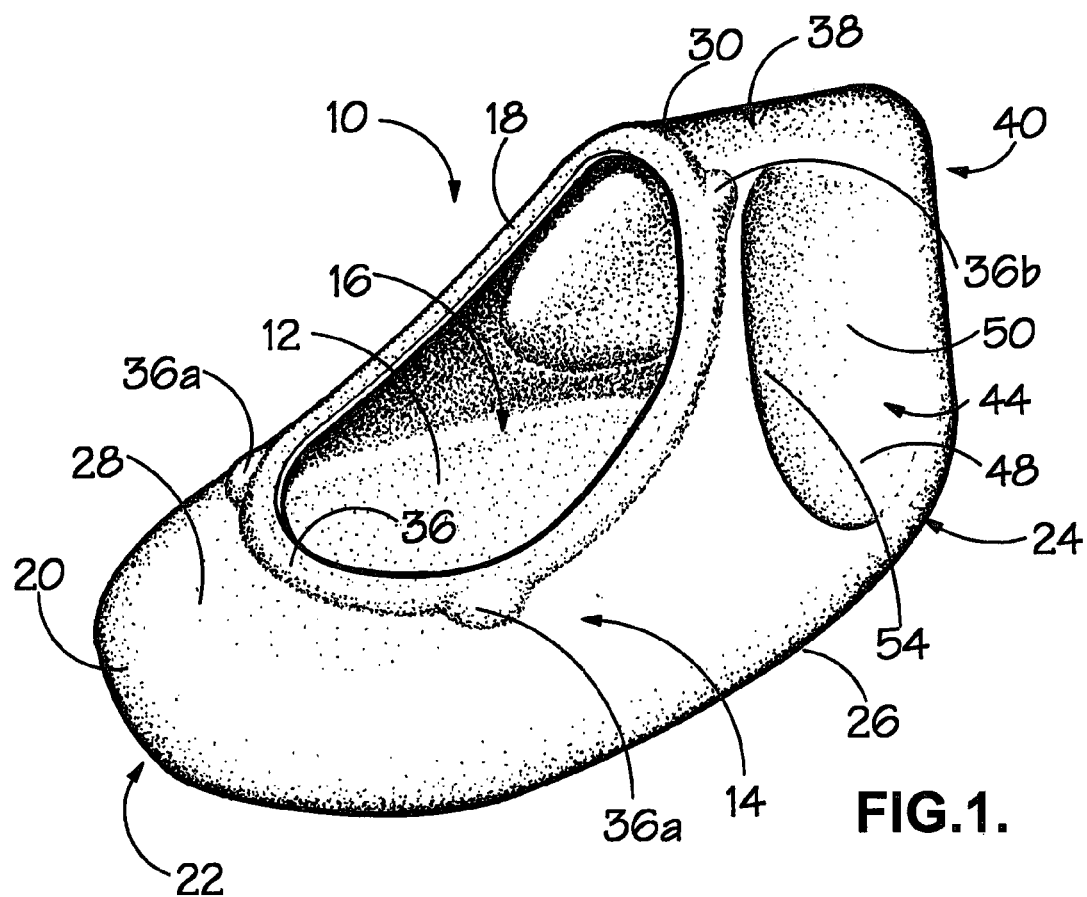
FIG. 1 is a perspective view from above of an embodiment of female urine bottle in accordance with the present invention.

An elongate disposable female urine bottle 10, is formed from a moulded and dried paper pulp on a conventional vacuum forming apparatus. The bottle 10 comprises a generally flat, planar base wall 12 on which the bottle rests, in use, and an enclosing wall 14 extending upwardly from the periphery of the base wall 12. The base wall 12 and the enclosing wall 14 together define a receiving volume 16 to which access is gained via an upwardly open aperture 18 in an upper face of the enclosing wall, as will be explained. As will be seen from the drawings, the base wall 12 and the enclosing wall 14 merge smoothly into each other to form a rounded corner 20 around the periphery of the base wall 12 and the lower periphery of the enclosing wall 14.

Figure 2:
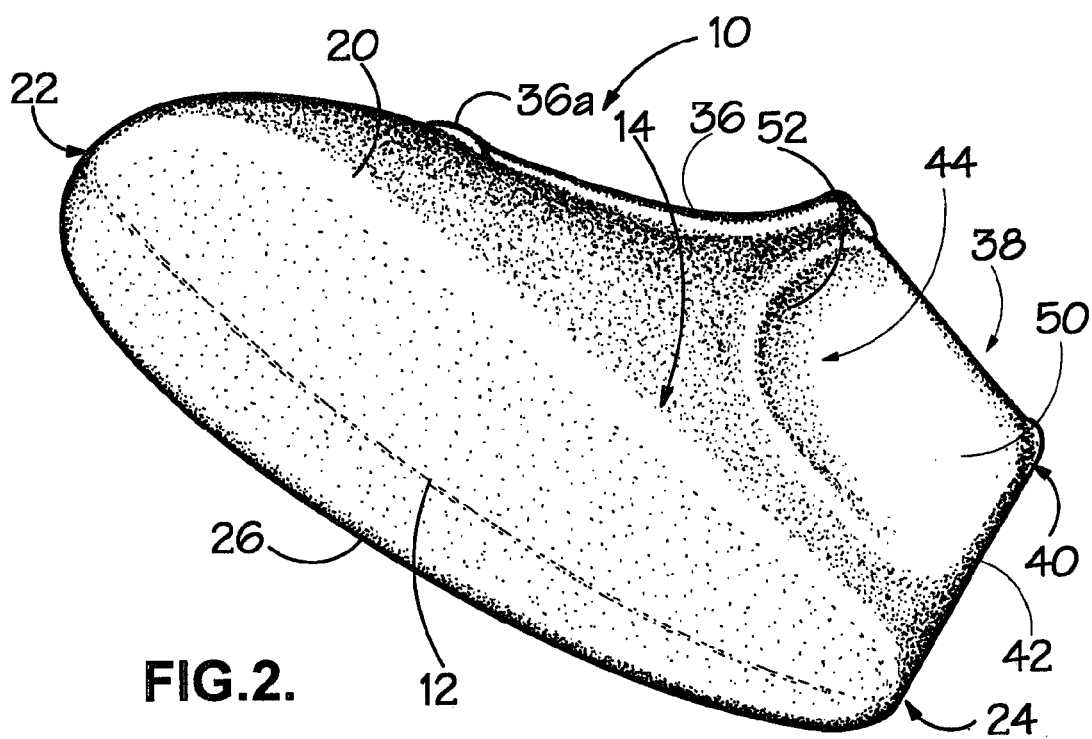
FIG. 2 is a perspective view from below of the female urine bottle of FIG. 1.
Figure 3:
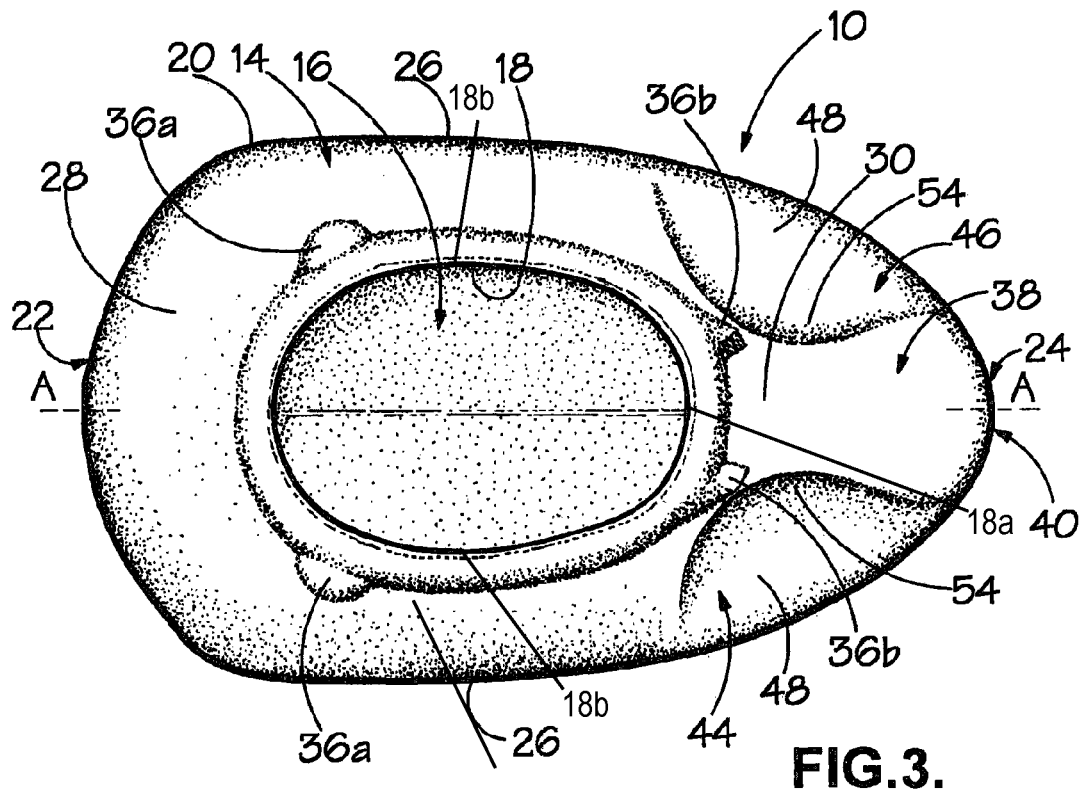
FIG. 3 is a plan view of the female urine bottle of FIG. 1.

As best seen in FIGS. 2 and 3, the base wall 12 is elongate and generally tear-shaped, having a wider, curved, rounded front end portion 22 which is presented to a user and a narrower, curved rounded rear end portion 24. The base wall 12 is symmetrical about an elongate axis A-A extending between the centres of the front and rear rounded end portions 22, 24. The two sides of the base wall 12 each comprise a generally straight portion 26, which merges smoothly at one end with the curved front portion 22 and merges smoothly at the opposite end, over a longer distance, with the curved rear portion 24. Although the base wall 12 is generally planar, it will be appreciated that it is slightly outwardly convex, in order to reduce the "concaving" process which takes place during the drying phase of the manufacturing process.

Figure 4:
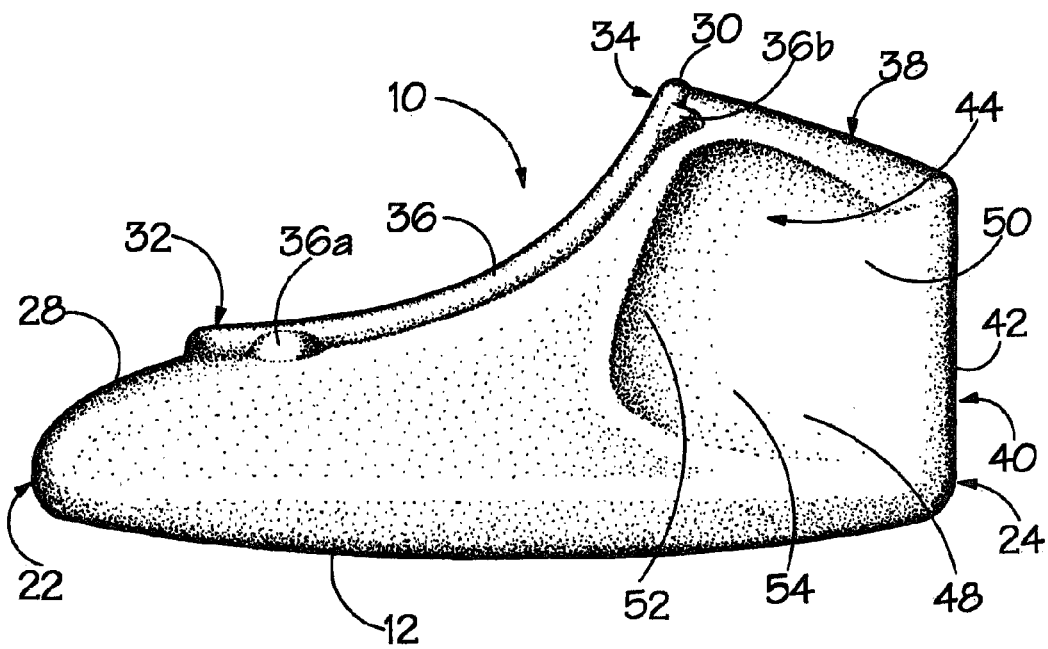
FIG. 4 is a side view of the female urine bottle of FIG. 1.
Figure 5:
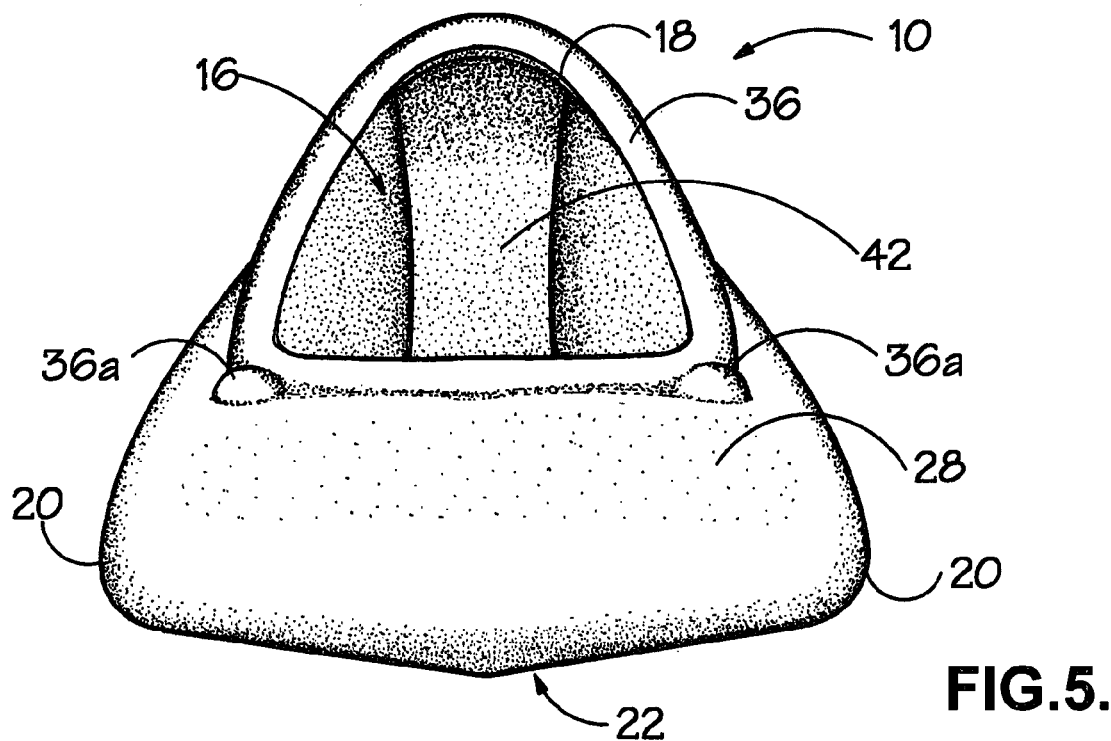
FIG. 5 is a front view of the female urine bottle of FIG. 1.
Figure 6:
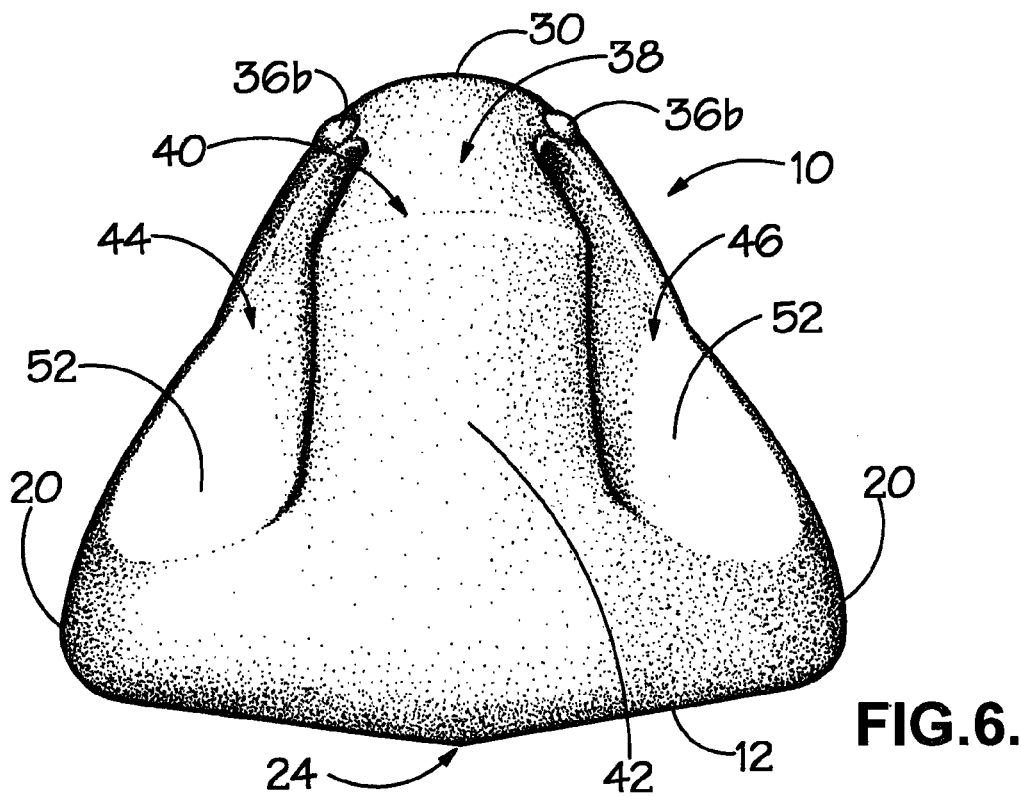
FIG. 6 is a rear view of the female urine bottle of FIG. 1.

As best seen in FIGS. 1 and 3, at the front end 22 of the bottle the enclosing wall 14 is turned back over the periphery of the base wall 12 to form a rounded overhang portion 28. The enclosing wall also increases in height from the wider, front portion 22 to the narrower, rear portion 24, reaching a maximum height at a point 30 around three-quarters of the way from the front to the rear of the base wall 12. The overhang 28 is located above the base wall 12 and extends rearwardly to the frontmost and lowermost portion of the aperture 18. As best seen in FIG. 3, the overhang also extends to both sides 18b of the aperture 18 and in fact extends continuously from the sides 18b of the aperture and the front end of the aperture. As best seen in FIGS. 4 to 6, the overhang 28 of the enclosing wall is also substantially perpendicular to the base wall 12 where it meets the base wall.

The access aperture 18 extends from the overhang 28 over the front of the base wall 12 to the highest point 30 and as best seen in FIG. 3 it is located above the base wall 12, i.e. the base wall 12 is visible through the aperture from above. The aperture 18 is generally oval when viewed from above (FIG. 3) but when viewed from the side (FIG. 4) is upwardly and forwardly concave, varying from a near-horizontal front portion 32 to a near-vertical rear portion 34. An outwardly and upwardly projecting lip 36 is also moulded around the whole of the periphery of the aperture 18, to assist in preventing spillage from the bottle and to improve the comfort of the bottle to a user, as will be explained.

The lip 36 is also provided with two stiffening projections 36 a on either side of the lower portion of the aperture 18 and two stiffening projections 36 b on either side of the upper portion 18a of the aperture 18. These are formed during moulding of the bottle in order to reduce tearing of the bottle during moulding and to increase the strength to the finished product.

The aperture is much wider than the aperture of known female urine bottles, which makes the bottle comfortable and stable in use and also reduces the likelihood of spillage or leakage of urine during use. In the illustrated embodiment the maximum width of the aperture is approximately 57% of the maximum width of the base wall 12. However, it has been found that the benefits are achieved if the maximum width of the aperture is at least half (50%) of the maximum width of the base wall 12.

Rearwardly of the aperture 18, the enclosing wall is formed into an enclosed roof portion 38 and into a handle portion 40 located at one end of the bottle. The roof portion 38 is located above the base wall 12, whereby the aperture 18 is located towards, and is open towards, the front end 22 of the bottle and does not extend to the rear end portion 24 of the bottle. The roof portion 38 slopes downwardly from its highest point 30 to the handle portion 40. The handle portion 40 is formed from a rear wall portion 42 of the enclosing wall, extending perpendicularly with respect to the planar base wall 12 from the periphery of the rounded rear portion 24 to the rearmost end of the roof portion 38, and two recesses 44, 46 in the enclosing wall 14 in front of the wall portion 42 on opposite sides of the rear wall portion 42. The recesses 44, 46 are mirror images of each other, to allow left- or right-handed operation, as will be explained.

As seen from the Figures, the recesses 44, 46 each comprises a generally triangular and planar face 48, extending upwardly aid inwardly from the upper boundary of the overhang 28 above the lateral portion of the rounded rear portion 24 of the base wall 12, a generally triangular and planar rear face 50 extending forwardly from the rear wall portion 42 and a generally triangular and planar front face 52 extending rearwardly from a position just behind the aperture 18. The three faces 48, 50, 52 merge smoothly into and with one another and into and with the adjacent portions of the enclosing wall 14 and converge at a rounded apex 54.

The urine bottle 10 is intended for use by a female patient in bed, who will thus be lying down or in a semi-recumbent position. The bottle can be easily grasped, either by the patient or by a nurse or other helper, by gripping the handle portion 40, whereby the person's thumb is received in one of the apertures, 44, 46 the fingers are wrapped around the upstanding end wall portion 42 and the end of the fingers are received in the other aperture 44,46. This provides a very secure means of lifting the bottle and the provision of the recesses 44, 46 as mirror images of one another allows the bottle to be lifted easily by both left- and right-handed people.

The bottle 10 is then offered to the patient, front end 22 first, and placed in position on the patient's bed. The wide and generally planar base 12 makes the bottle very stable and the very low height of the front portion of the bottle facilitates correct positioning of the bottle, particularly if the patient has restricted mobility.

The generally oval shape of the aperture 18, and the upwardly and forwardly concave shape of the profile of the periphery of the aperture 18 (i.e. when viewed from the side) conform generally to the shape of the user's body and the engagement of the upstanding lip 36 with a user's body helps to from a seal between the bottle and the user's body, thereby reducing the likelihood of leakage of urine. It will also be observed that the aperture 18 is relatively wide, thereby further reducing the likelihood of leakage.

After use, the bottle is then removed from the patient for disposal, typically in a conventional macerator. This is facilitated by the handle portion 40 as described previously. It will also be observed that the overhang 28 of the enclosing wall 14 around the lower portions of the aperture 18 reduces the likelihood of spillage of urine from the bottle during transport. Furthermore, the enclosed roof portion 38 located rearwardly of the aperture 18 above the base wall 12 allows the bottle to be tilted rearwardly during transport, whereby the liquid in the bottle collects in the rear of the receiving volume, adjacent the vertical wall portion 42, the recesses 44, 46 and the roof portion 38, and away from the aperture 18, thereby further reducing the likelihood of spillage during transport.

The invention is not restricted to the details of the foregoing embodiment. For example, although the bottle of the described embodiment is made from dried, moulded paper pulp, other materials could be used. For example, if it is intended to have a reusable bottle rather than a disposable bottle, the bottle may be formed from a reusable, washable and/or autoclavable material such as plastics.

The invention claimed is:

1. A urine bottle formed from maceratable dried moulded paper pulp, comprising:
    a flat, generally planar base wall on which the bottle rests, in use;
    an enclosing wall extending upwardly from the base wall;
    a urine receiving volume defined by the base wall and the enclosing wall; and
    a single aperture in the enclosing wall which allows access to the urine receiving volume;
    the urine bottle being elongate and comprising a front end portion for presentation to a user and a rear end portion, the front end portion being wider than the rear end portion, the aperture being wider at the front end portion than the rear end portion, such that a width of the aperture continuously narrows as the aperture extends from the front end portion to the rear end portion;
    the enclosing wall comprising:
        a front wall portion which overhangs the base wall at the front end portion of the bottle and extends rearwardly to the aperture and is located above the base wall;
        two side wall portions;
        a top wall portion located above the base wall extending between the two side wall portions and located rearwardly of the aperture;
        handle means comprising a recess in each of the two side wall portions, located below the top wall portion and forwardly of the rear end portion;
        one or more stiffening projections along the lower portion of the periphery of the aperture; and
        one or more additional stiffening projections along the upper portion of the periphery of the aperture, wherein the stiffening projections along the lower portion of the periphery of the aperture are thicker than the additional stiffening projections along the upper portion of the periphery of the aperture.

2. The urine bottle of claim 1, wherein the handle means are located at the rear end portion.

3. The urine bottle of claim 2, wherein the handle means comprises a rear wall portion of the enclosing wall.

4. The wine bottle of claim 3, wherein the base wall is planar and the rear wall portion of the enclosing wall which forms part of the handle means extends perpendicularly to the base wall.

5. The urine bottle of claim 1, wherein the recesses in the two side wall portions are mirror images of each other.

6. The urine bottle of claim 2, wherein the handle means further comprises the top wall portion of the enclosing wall.

7. The urine bottle of claim 6, wherein the top wall portion extends towards the aperture.

8. The urine bottle of claim 7, wherein the top wall portion extends towards an upper end of the aperture.

9. The urine bottle of claim 1, wherein the portion of the enclosing wall which overhangs the base wall at the front end of the bottle extends rearwardly to the front portion of the periphery of the aperture.

10. The urine bottle of claim 9, wherein the enclosing wall comprises a portion which overhangs the base wall at the front and side portions of the aperture.

11. The urine bottle of claim 1, wherein the base wall is planar and the frontmost portion of the enclosing wall meets the base wall perpendicularly.

12. The urine bottle of claim 1, wherein each overhanging portion is rounded.

13. The urine bottle of claim 1, wherein the maximum length of the base wall is at least four times as long as the maximum length of the portion of the enclosing wall which overhangs the base wall at the front end of the bottle.

14. The urine bottle of claim 1, wherein the urine bottle is elongate and the width of the aperture at its widest point is at least half the width of the base wall at its widest point.

15. The urine bottle of claim 1, the base wall being planar, the aperture being upwardly concave when viewed from the side and the lowermost portion of the aperture being parallel into the base wall.

16. The urine bottle of claim 1, the aperture being elongate in plat view and comprising front and rear ends and sides joining the front and rear ends, the enclosing wall extending outwardly from the sides and the front end of the aperture.

17. The urine bottle of claim 16, wherein the enclosing wall extends outwardly from the sides and front end of the aperture and downwardly to meet the base wall.

18. The wine bottle of claim 1, herein the aperture is upwardly and forwardly concave when viewed from the side.

19. The urine bottle of claim 1, wherein the aperture is located above the base wall.

20. The urine bottle of claim 1, wherein the enclosing wall comprises a portion which is located above the base wall rearwardly of the aperture.

21. A urine bottle formed from maceratable dried moulded paper pulp, comprising:
   a flat, generally planar base wall on which the bottle rests, in use;
   an enclosing wall extending upwardly from the base wall;
   a urine receiving volume defined by the base wall and the enclosing wall; and
   a single aperture in the enclosing wall which allows access to the urine receiving volume;
   the urine bottle being elongate and comprising a front end portion for presentation to a user and a rear end portion, the front end portion being wider than the rear end portion, the aperture being wider at the front end portion than the rear end portion, such that a width of the aperture continuously narrows as the aperture extends from the front end portion to the rear end portion;
   the enclosing wall comprising:
      a front wall portion which overhangs the base wall at the front end portion of the bottle and extends rearwardly to the aperture and is located directly above the base wall;
      two side wall portions;
      a top wall portion located above the base wall extending between the two side wall portions and located rearwardly of the aperture;
      handle means comprising a recess in each of the two side wall portions, located below the top wall portion and forwardly of the rear end portion;
      one or more stiffening projections along the lower portion of the periphery of the aperture; and
      one or more additional stiffening projections along the upper portion of the periphery of the aperture, wherein the stiffening projections along the lower portion of the periphery of the aperture are thicker than the additional stiffening projections along the upper portion of the periphery of the aperture.

22. The urine bottle of claim 1, wherein:
   the stiffening projections along the lower portion of the periphery of the aperture comprise a pair of stiffening projections on either side of the lower portion of the aperture; and
   the additional stiffening projections along the upper portion of the periphery of the aperture comprise an additional pair of stiffening projections on either side of the upper portion of the aperture.

\* \* \* \* \*